United States Patent [19]

Pease et al.

[11] Patent Number: 5,039,818

[45] Date of Patent: * Aug. 13, 1991

[54] SQUARAINE DYE

[75] Inventors: John Pease, Los Altos; Thomas L. Tarnowski, San Francisco; Donald Berger, San Jose; Chiu C. Chang, Sunnyvale, all of Calif.

[73] Assignee: Syntex (U.S.A.) Inc., Palo Alto, Calif.

[*] Notice: The portion of the term of this patent subsequent to Feb. 21, 2006 has been disclaimed.

[21] Appl. No.: 300,996

[22] Filed: Jan. 23, 1989

Related U.S. Application Data

[62] Division of Ser. No. 834,168, Feb. 27, 1986, Pat. No. 4,830,786.

[51] Int. Cl.$^5$ .......................................... C07D 403/08
[52] U.S. Cl. .................................. 548/409; 548/455
[58] Field of Search ............................. 548/409, 455

[56] References Cited

U.S. PATENT DOCUMENTS 4,806,488  2/1989  Berger, Jr. et al. ................ 436/536

OTHER PUBLICATIONS

Treibs et al., Liebigs Ann. Chem. 712 (1968), pp. 123–187.
Treibs et al., Liebigs Ann. Chem. 699 (1966), pp. 153–167.
Chem Abstracts, vol. 71, No. 8 (1969), Abst. No. 31354p.

*Primary Examiner*—Joseph Paul Brust
*Assistant Examiner*—Jacqueline Haley
*Attorney, Agent, or Firm*—Theodore J. Leitereg; Linda J. Nyari

[57] ABSTRACT

Squaraine dyes and compositions of matter containing such dyes are disclosed. The squaraine dyes have an absorption maximum greater than 600 nanometers and are particularly useful in conjunction with a helium/neon (He/Ne) laser. Some of the squaraine dyes are hydrophilic and are therefore water soluble or water compatible and others of the squaraine dyes are lipophilic.

4 Claims, No Drawings

SQUARAINE DYE

This is a division of application Ser. No. 06/834,168, filed Feb. 27, 1986, now U.S. Pat. No. 4,830,786, incorporated herein by reference.

BACKGROUND OF THE INVENTION

1. Field of the Invention

This invention relates to squaraine dyes and compositions of matter containing such squaraine dyes. Squaraine dyes have a structural element of cyclobutenolate, generally being a condensation product of squaric acid (dihydroxycyclobutenedione) and an active compound such as a pyrrole or an aniline. Squaraine dyes have been found to have a number of uses based on their unique properties. One such use involves layered photo responsive imaging devices. Such devices are responsive to visible light and infrared illumination needed for laser printing.

Many of the known squaraine dyes are fluorescent compounds absorbing light in the wavelength region of from about 400 to about 1000 nanometers. Consequently, another use that has been proposed for squaraine dyes is in the area of assays. Fluorescent compounds have achieved wide application in assays because of their ability to emit light upon excitation with energy within certain energy ranges. By virtue of this ability, fluoescers have found employment as labels in chemical or biological processes. Various compounds can be conjugated to fluorescent compounds, the conjugate subjected to some type of partitioning, and the fate of the conjugate determined by irradiating the sample with light and deteting the zone in which the conjugate exists. Fluorescent labels find use in immunoassays, involving specific binding pairs, such as ligands and receptors, for example, antigens and antibodies. For such use, the fluorescent compounds preferably are soluble in an aqueous medium or at least water compatible.

Another use of fluorescent compounds is to incorporate such compound into a cell wall or a liposome. The cell or the liposome with the fluorescent compound incorporated therein an also be employed in assays. For example, dyes incorporated into cell membranes are useful in the area of blood typing where a change in fluorescence as a result of agglutination of cells is determined. Liposomes containing fluorescent dyes also find use in the assay area, particularly in immunoassays. For this purpose it is desirable that the fluorescent dyes be lipophilic.

Laser beams find use in the assay area as means for irradiating a fluorescent compound. In the field of assays it is important to avoid contributions to a signal produced in relation to the amount of analyte, which contributions result from other than the analyte. For example, serum or plasma from a patient is often used to conduct the assay. Serum is itself fluorescent. The materials that cause fluorescence in serum or plasma normally absorb light at a wavelength below 600 nanometers. Therefore, it is desirable to employ fluorescent dyes in fluorescent assays that have an absorption maximum greater than 600 nanometers. It is also desirable to employ a laser beam to provide the souce of energy for activation of the fluorescent dye. One such laser is the helium/neon laser which emits light at 633 nanometers.

2Description of the Related Art

Various squarate dyes are discussed by Sprenger, et al., *Angew. Chem*, 80, 541 (1968); Sprenger, et. al., *Angew. Chem.*, 79; 581, 1967; Sprenger, et al., *Angew. Chem. Internat. Edit.* , 5:894, 1966; and Maaks, et al., ibid., 5:888, 1966.

Novel unsymmetrical squaraine systems are disclosed in U.S. Pat. No. 4,521,621. A process for the preparation of squaraine compositions in the presence of an amine component is disclosed in U.S. Pat. No. 4,524,220. A process for preparation of squaraine compositions is disclosed in U.S. pat. No. 4,525,592. A process for preparation of squaraine compositions from half esters of squaric acid is disclosed in U.S. Pat. No. 4,524,219. Processes for the preparation of squaraine compositions are described in U.S. Pat. No. 4,524,218. A process for the recovery of high purity squaric acid is described in U.S. Pat. No. 4,523,980. Amine derivatives of squaric acid are described in U.S. Pat. Nos. 4,123,270, 4,353,971, 3,838,095, and 3,824,099.

SUMMARY OF THE INVENTION

The present invention concerns novel compounds that are squaraine dyes and novel compositions containing such dyes. The novel squaraine dyes of the invention have an absorption maximum greater than 600 nanometers. Some of the squaraine dyes are hydrophilic and therefore water compatible or water soluble. Other squaraine dyes of the invention are lipophilic.

DESCRIPTION OF THE SPECIFIC EMBODIMENTS

Generally, the novel squaraine dyes of the invention have the following formula

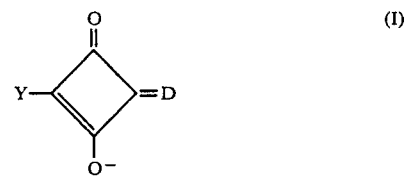

wherein:

D is independently selected from the group consisting of

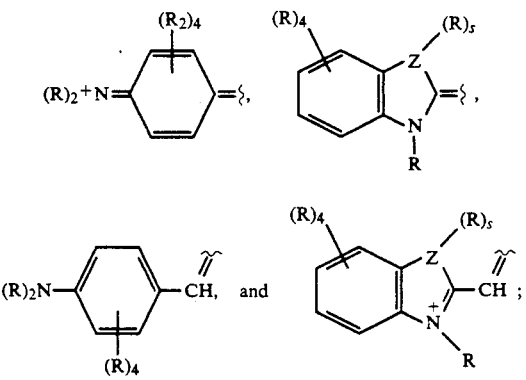

Y is independently selected from the group consisting of

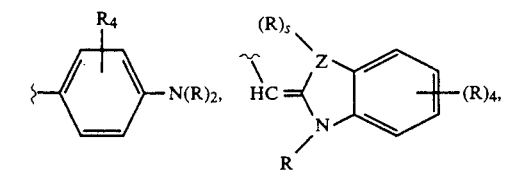

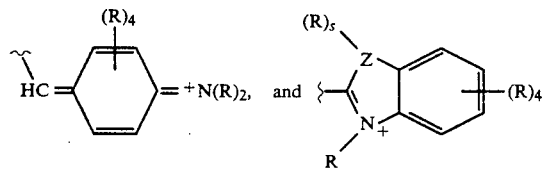

Z in D and Z in Y are independently selected from the group consisting of carbon, nitrogen, oxygen, sulfur, and selenium;

s is 2 when Z is carbon, 1 when Z is nitrogen, and 0 when Z is oxygen, sulfur, or selenium;

R is independently hydrogen or a substituent having from 1 to 30 atoms other than hydrogen, which atoms are selected from the group consisting of carbon, oxygen, nitrogen, sulfur, halogen of atomic number 9 to 53, boron with the proviso that, where D and Y are the same and all but one R group is lower alkyl (1 to 4 carbon atoms), the remaining R group has at least one heteroatom such as, for example, oxygen, nitrogen, or sulfur, or is a chain of at least five carbon atoms which may or may not have such heteroatom; R may be takn together with one or more other R groups to form one or more rings, usually five or six membered rings; R may contain one or more groups which are hydroxy, carboxy, including esters and amides thereof, sulfonic acid, amine including primary, secondary, and tertiary amine, aryl including phenyl, carbamate, succinimidyl and the like.

Preferred compounds of the present invention have the following formula

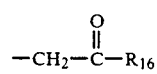
(II)

wherein:

$R_1$ and $R_4$ are independently selected from the group consisting of lower alkyl (1 to 4 carbon atoms);

$R_2$ and $R_3$ are independently selected from the group consisting of (a) lower alkyl (1 to 4 carbon atoms), (b) alkyl of from 5 to 20 carbon atoms, preferably 10 to 16 carbon atoms, including cycloalkyl, and (c)

$$-CH_2-\overset{O}{\underset{\|}{C}}-R_{16}$$

wherein. $R_{16}$ is hydroxyl, or lower alkoxy (1 to 4 carbon atom), or $-NH_2NH_2$ and salts thereof, or $-NH(CH_2)_cNH_2$ and salts thereof, c is 1 to 5, or

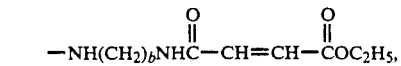

d is 1 to 5, or

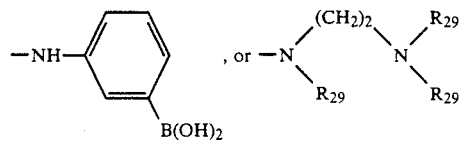

b is 1 to 5, or $-NH(CH_2)_t-S-S-CH_3$ wherein t is 1 to 5, or

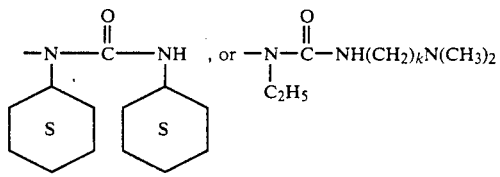

wherein $R_{29}$ is

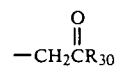

wherein $R_{30}$ is lower alkyl (1 to 4 carbon atoms), or

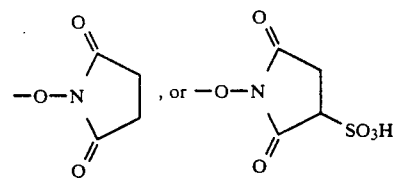

wherein k is 1 to 5, or lower alkoxy (1 to 4 carbon atoms), or

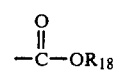

and salts thereof, or dioleoylphosphotidylethanolamine, or $-NH(CH_2)_nNHR_{17}$ wherein $R_{17}$ is $$-\overset{O}{\underset{\|}{C}}-OR_{18}$$

wherein $R_{18}$ is lower alkyl (1 to 4 carbon atoms); $-(CH_2)_rNH_2$ wherein r is 1 to 5; hydrogen including acid salts thereof;

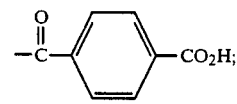

and n is 1 to 5, preferably 2 to 3, or —NH(CH$_2$-)$_p$—R$_{19}$ wherein R$_{19}$ is

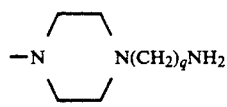

wherein q is 1 to 5; —NH$_2$; pehnyl, amino substituted phenyl; and p is 1 to 15, preferably 2 to 12, and R$_5$ and R$_6$ are independently selected from the group consisting of hydrogen, hydroxyl, lower alkoxyl (1 to 4 carbon atoms), alkoxyl of from 5 to 20 carbon atoms,

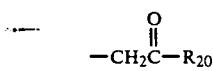

wherein R$_{20}$ is hydrogen or lower alkoxyl (1 to 4 carbon atoms); with the proviso that only one of R$_2$ or R$_3$ is lower alkyl (1 to 4 carbon atoms) when R$_5$ and R$_6$ are both hydroxyl or both hydrogen; and

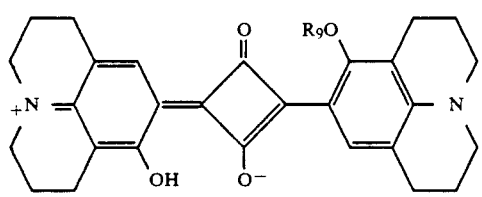 (III)

wherein

R$_9$ is hydrogen, lower alkyl (1 to 4 carbon atoms) or —CH$_2$(CHhd 2)$_w$SO$_3$H wherein w is 1 to 5, preferably 2 to 3; and

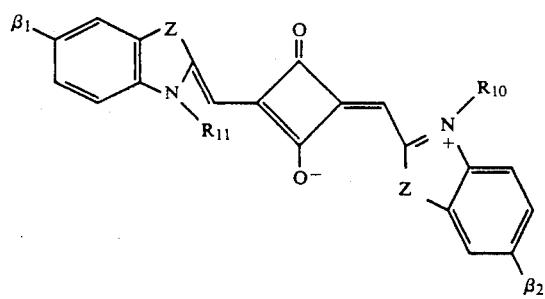 (IV)

wherein:

Z' is 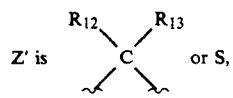 or S,

Z' is 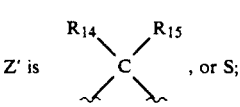, or S;

R$_{12}$, R$_3$, R$_{14}$, and R$_{15}$ are independently hydrogen, lower alkyl (1 to 4 carbon atoms) or R$_{12}$, R$_{13}$ and R$_{14}$, R$_{15}$ are taken together to form

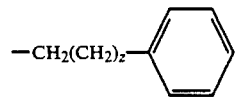

R$_{10}$ and R$_{11}$ are independently selected from the group consisting of hydrogen, lower alkyl (1 to 4 carbon atoms), alkyl of from 5 to 20 carbon atoms, including cycloalkyl,

wherein z is 0 to 5,

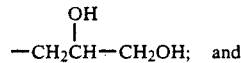

wherein R$_{21}$ is hydrogen, or lower alkyl (1 to 4 carbon atoms) and v is 0 to 5, and —CH$_2$CH(OH)—CH$_2$OH; and $\beta_1$ and $\beta_2$ are independently hydrogen, halogen (chlorine, bromine, fluorine), or lower alkoxy (1 to 4) carbon atoms), with the proviso that only one of $\beta_1$ or $\beta_2$ is hydrogen or halogen when R$_{10}$ and R$_{11}$ are both hydrogen or lower alkyl of 1 or 2 carbon atoms; and

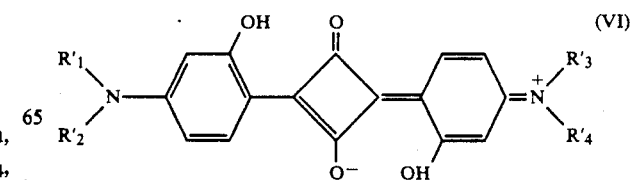 (V)

wherein:

R$_{22}$, R$_{23}$, and R$_{25}$ are independently hydrogne, lower alkyl (1 to 4 carbon atoms), or alkyl of from 5 to 20, preferably 10 to 16, carbon atoms, and R$_{24}$, R$_{26}$, R$_{27}$, and R$_{28}$ are independently hydrogen, lower alkyl (1 to 4 carbon atoms), alkyl of from 5 to 20, preferably 10 to 16, carbon atoms, hydroxyl, lower alkoxyl (1 to 4 carbon atoms), or alkoxyl of from 5 to 20, preferably 10 to 16, carbon atoms.

Particularly preferred compounds of the present invention have the following formulas wherein
(a) R′₁, R′₂, R′₃, and R′₄ are all
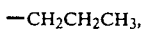 (i)
 (ii)
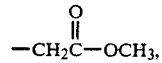 (iii)
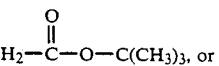 (iv)
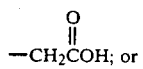 (v)
(b) R′₁ and R′₄ are both —CH₂CH₃ and R′₂ and R′₃ are both
—CH₂(CH₂)₄CH₃, (i′)
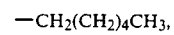 (i)
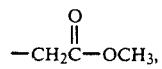 (ii)
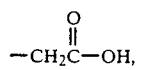 (iii)
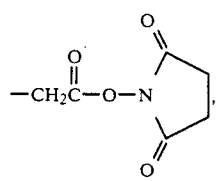 (iv)
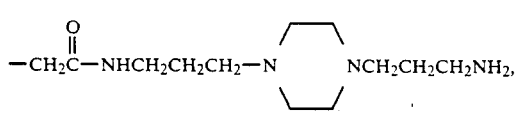 (v)
 (vi)
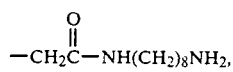 (vii)
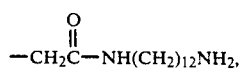 (viii)
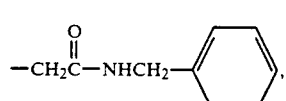 (ix)
dioleoylphosphotidyl ethanolamine, (x)
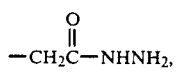 (xi)
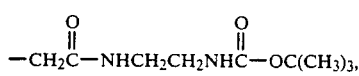 (xii)
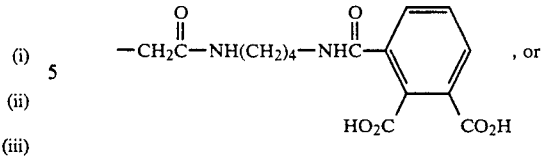 (xiii)
 (xiv)
(c) R′₁, R′₂, and R′₃ are all —CH₂CH₃ ad R′₄ is
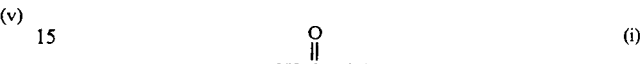 (i)
 (ii)
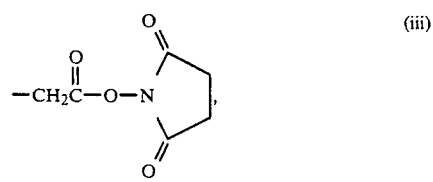 (iii)
 (iv)
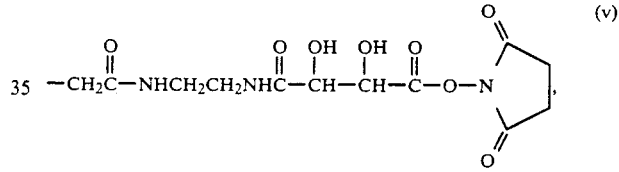 (v)
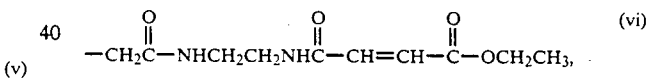 (vi)
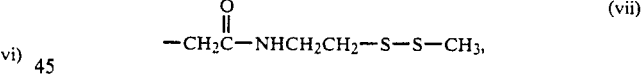 (vii)
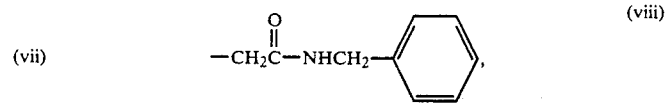 (viii)
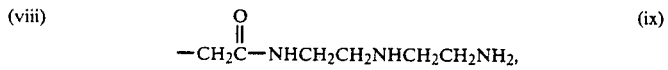 (ix)
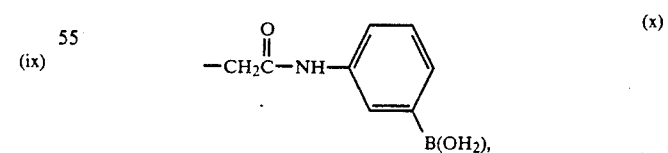 (x)
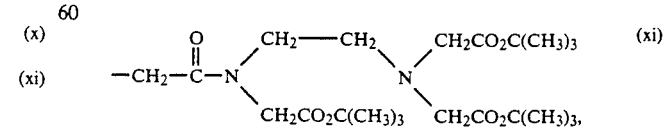 (xi)
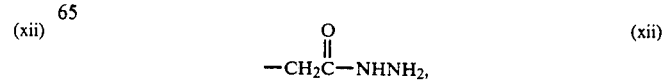 (xii)

-continued

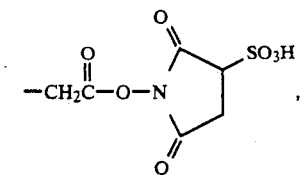

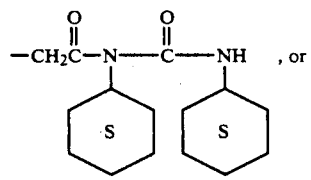

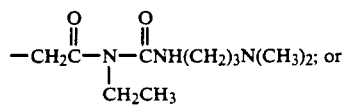

(d) R′₁ and R′₂ are —CH(CH₂)₂CH₃, R′₃ is —CH₂CH₃, and R′₄ is

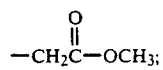

*(e) R′₁ and R′₂ are —CH₂(CH₂)₁₄CH₃, R′₃ is —CH₂CH₃, and R′₄ is

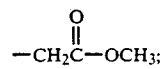

(f) R′₁ and R′₂ are —CH₂(CH₂)₂CH₃, R′₃ is —CH₂CH₃, and R′₄ is

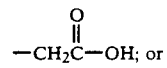

(g) R′₁ and R′₂ are —CH₂(CH₂)₁₄CH₃, R′₃ is —CH₂CH₃, and R′₄ is

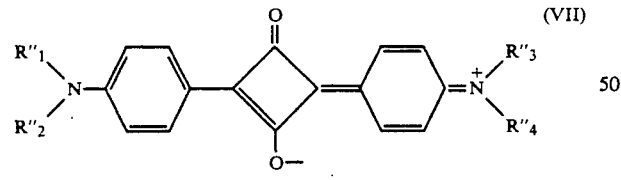

wherein R″₁, R′₂, R″₃ and R″₄ are all —CH₂(CH₂)₁₄₅CH₃; and

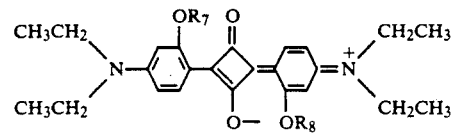

wherein:
(a) R″₇ and R″₈ are —CH₂(CH₂)₁₄CH₃;
(b) R″₇ is hydrogen and R″₈ is —CH₃;
(c) R″₇ is hydrogen and R₈ is

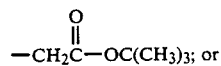

(d) R″₇ is hydrogen and R″₈ is

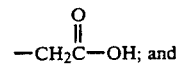

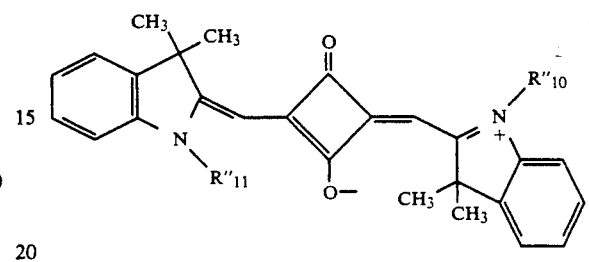

wherein:
(a) R₁₀ and R₁₁ are both
(i)—CH₂(CH₂)₂CH₃,
(ii)—CH₂(CH₂)₄CH₃,
(iii)—CH₂(CH₂)₅CH₃,
(iv)—CH₂(CH₂)₆CH₃,
(v)—CH₂(CH₂)₁₀CH₃,
(vi)—CH₂(CH₂)₁₄CH₃,

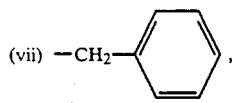

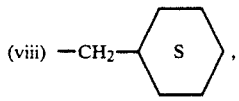

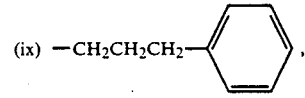

(x) —CH₂CH₂C(=O)—OCH₂CH₃, (xi) —CH₂C(=O)—OC(CH₃)₃, (xii) —CH₂COOH, (xiii) —CH₂CH₂C(=O)—OH, (xiv) —CH₂CH(OH)—CH₂Cl, (xv) —CH₂CH(OH)CH₂—S—CH₂CH(OH)—CH(OH)—CH₂—S—S—CH₃, or (xvi) —CH₂CH₂CH₂C(=O)—OCH₂CH₃; or

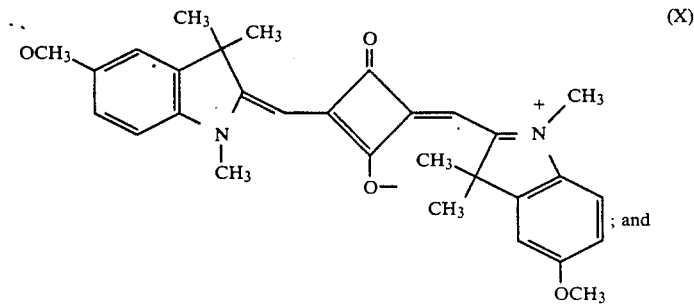

(X)

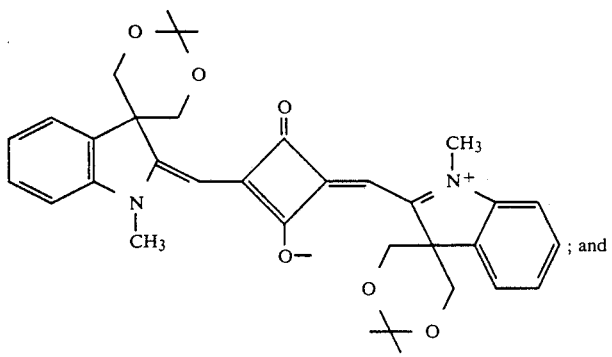

(XI)

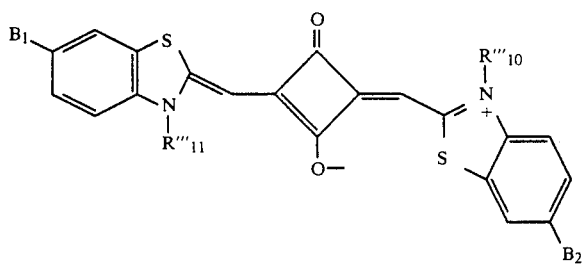

(XII)

wherein:
(a) R'''₁₀ and R'''₁₁ are —CH₂(CH₂)₂CH₃ and β₁ and β₂ are hydrogen; or
(b) R'''₁₀ and R'''₁₁ are —CH₂(CH₂)₁₄CH₃ and β₁ and β₂ are hydrogen; or
(c) R'''₁₀ and R'''₁₁ are —CH₂CH₃ and β₁ and β₂ are —OCH₂CH₃; and

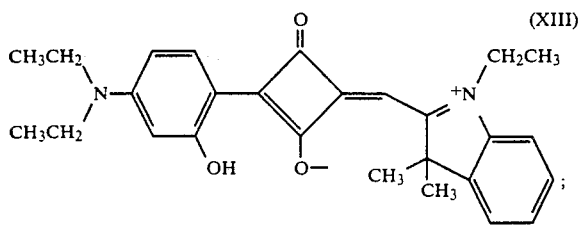

(XIII)

and (XIV)

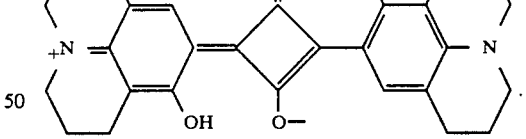

wherein R'₉ is hydrogen or (b) —CH₂CH₂CH₂SO₃H

It will be appreciated by those skilled in the art that those compounds mentioned above which have a polar or polar grups such as hydroxyl, amine, carboxy, sulfonic acid and the like will be hydrophilic or at least water compatible. Furthermore, it will be appreciated by those skilled in the art that those compounds mentioned above that lack such polar gorups will tend to be lipophilic in character.

The compounds of the present invention can be prepared by a reaction sequence, some or all of the individual steps of which are separately known in the art. Some of the squaraine dyes of the present invention can be made according to procedures similar to those described by Sprenger et al., *Angew. Chem.*, 80, 541 (1968); Springer et al., *Angew. Chem*, 79, 581 (1967); Sprenger et al., *Angew. Chem., Internat. Edit.*, 5, 894 (1966); and Maaks et al., *Angew. Chem. Internat. Edit.*, 5, 888 (1966). In general, squaric acid (dihydroxycyclobutenedione) is condensed with an active compound such as a pyrrole or an aniline. The condensation is conducted under conditions for removing water from the reaction mixture. For example, the condensation can be carried out under rflux in an alkanol/benzene solvent mixture. The rsulting product can be collected and purified by, for example, recrystallization, distillation, chromatography, or the like. The group or functionality imparting hydrophilicity or lipophilicity to a particular compound of the invention can be part of an initial reactant for the condensation or it can be introduced after the condensation by conventional techniques.

The squaraine dyes of the invention can be conjugated to specific binding pair (sbp) members such as antigens and antibodies by techniques that are known in the art. Such conjugation can be the result of direct bond formation between the squaraine dye and the sbp member. On the other hand, a linking group as described above can be introduced into the squaraine dye or the sbp member for attachment to the other component. A functionality for attachment such as carboxylic acid, hydroxyl, thio, amino, aldehydic, amido, activated ethylenes such as maleimide, sulfonic acids, and the like can be introduced into the squarate dye or the sbp member if such functionality is not originally present in the dye or the sbp member. Methods of conjugation involving sbp members are described in, e.g., U.S. Pat. No. 3,817,837, the disclosures of which is incorporated herein by reference.

Some of the compounds of the invention have properties that are very desirable for their use in assays. The compounds have a high extinction coefficient, a high quantum efficiency, approaching one, chemical stability, and satisfactory Stokes shift. Furthermore, where the compounds are to be used in the presence of serum or other composition, which is in itself fluorescent, the compounds absorb energy in a substantially different range from that absorbed by the other compounds in the medium. As mentioned above, the present compounds have an absorption maximum greater than 600 nanometers.

Some of the compounds of the invention are useful because of their lipophilic character. For example, lipophilic squaraine dyes of the invention may be incorporated into a cell and thereby cause the cell to become fluorescent. Because of their lipophilic character some of the squaraine dyes may be employed in the formation of liposomes wherein the lipophilic material is incorporated into the liposome.

Generally the molar extinction coefficient for the novel squaraine dyes at the wavelength of the exciting light is greater than 1,000 and often greater than 10,000 per mole per centimeter. The novel squaraine dyes have a high quantum yield, normally greater than 0.05 and often greater than 0.3.

EXAMPLES

The invention is further demonstrated by the following illustrative examples.

EXAMPLE 1

PREPARATION OF XIII

Twenty-five (25) ml of 50% n-butanol in benzene was dried by azeotropic distillation for thirty minutes under a nitrogen atmosphere. One mmol (165 mg) of N,N-diethyl-3-aminophenol, 1 mmol (114 mg) of 3,4-dihydroxy-3-cyclobutene-1,2-dione, and 1 mmol (315 mg) of N-ethyl-2,3,3-trimethylindolenium iodide were added and the reaction was refluxed under nitrogen for three hours with azeotropic removal of water. The reaction rapidly turned from a golden yellow color to green, then to deep blue. At the end of the reaction all solvents were evaporated off and the crude blue product was chromatographed on silica gel 60, using a gradient of methanol in chloroform to effect separation. 24 mg (6%) yeidl) of pure blue product was obtained ($\lambda$]max (DMSO):642 nm).

EXAMPLE 2

Preparation of VI(a)(Iv)

1,3-bis[4-(N,N-dicarboxymethylamino)-2-hydroxyphenyl]-2,4-dihydroxycyclobuteneliydium dihydroxide, bis (inner salt) tetra tert-butyl ester.

Twenty-five (25) nl of 50% n-butanol in benzene was dried by azeotropic distillation for thirty minutes under a nitrogen atmosphere; 1.18 mmol (400 mg) of 3-dicarboxymethylaminophenol di-tert-butyl ester and 0.59 mmol (68 mg) of 3,4-dihydroxy-3-cyclobutene-1,2-dione were added. The reaction mixture was refluxed under nitrogen for five hours with azeotropic removal of water. The reaction rapidly turned from a golden yellow color to light green, then to an inreasingly deeper blue-green. The product gradually precipitated from solution. After the reaction mixture cooled to room temperature, the deep blue-green solid product was filtered off and dried in vacuo. The reaction solvent was evaporated off and the remainder of the product was purified by preparative thin layer chromatography on silica gel 60 using $CHCl_3$ as a developing solvent. A total of 303 mg (68% yield) of pure compound was obtained ($\lambda$ max=642 nm).

EXAMPLE 3

Sixty-six (66) $\mu$ mol (50 mg) of compound VI(a)(iv) was dissolved in 10 ml of dry methylene chloride; 2 ml of dry trifluoroacetic acid was added. The reaction mixture was stirred at room temperature under nitrogen for 2.5 hours. The product precipitated out of solution and was filtered off and dried in vacuo. 32 mg (91% yield) of product was obtained, pure by thin layer chromatography and high performance liquid chromatograph ($\lambda$ max=534 nm in methanol).

EXAMPLE 4

Preparation of VIII(b), VIII(c) and VIII(d)

1-[4-(diethylamino)-2-hydroxyphenyl]-3-[4-diethylamino)-2-alkoxyphenyl]-2,4-dihydroxycyclobutenediylium dihydroxide, bis (inner salt)

These compounds were all prepared by the same method:

0.1 mmol (41 mg) of 1,3-bis[4-(diethylamino)-2-hydroxyphenyl]-2,4-dihydroxycyclobutenediylium dihydroxide, bis(inner salt) (DEAS) was reacted with 0.4 mmol of the appropriate alkyl halide (methyl iodide, t-butylbromoacetate, or bromoacetic acid) in the presence of 0.2 mmol of potassium tert-butoxide in 5 ml of dry dimethylformamide at room temperature under nitrogen for 15 hours. The reaction was worked up by pouring the deep blue DMF solution into 10 ml of water, extracting with 2×20 ml of ethyl acetate, washing the ethyl acetate phases with 1×20 ml of saturated brine, and combining and drying the organic phases over sodium sulfate. Following preparative thin layer chromatography on silica gel GF, using 10% methanol in chloroform as developing solvent, the desired product was obtained pure. Compound VIII (b) was obtained in 13% yield (λ max=652 nm). Compound VIII (c) was obtained in 24% yield. Compound VIII (d) was obtained in 25% yield (λ max=647 nm).

EXAMPLE 5

Preparation of IX(a)(xiv)

Twenty-five (25) ml of 50% n-butanol-toluene was dried by azeotropic distillation under a nitrogen atmosphere and 1 mmol (252 mg) of chloroindoline [prepared by the reaction of 2,3,3-trimethylindolenine with epichlorohydrin, neat, 100° C.] and 0.5 mmol (57 mg) of 3,4-dihydroxy-3-cyclobutene-1,2-dione were added. The reaction mixture was heated at reflux under nitrogen for two hours with azeotropic removal of water. The reaction rapidly turned from golden color to green to deep blue. The product crystallized out of the hot solution. After allowing the reaction to cool to room temperature, the pure product was filtered off; 152 mg (52% yield) of a pure green-blue solid was obtained. (λ (DMSO):646 nm)

EXAMPLE 6

Preparation of IX(a)(xv)

Twenty (20) ml of 50% n-butanol in benzene was dried by axeotropic distillation for thirty minutes under nitrogen and 0.35 mmol (40 mg) of 3,4-dihydroxy-3-cyclobutene-1,2-dione and 0.70 mmol (292 mg) of the indoline disulfide [prepared by the reaction of the chloroindoline of Example 5 with dithioerythritol according to standard procedures] were added. The reaction mixture was refluxed under nitrogen for two hours under nitrogen with azeotropic removal of water. Ther eaction rapidly turned from a yellow color to deep green, and then radually to deep blue. An additional 0.1 mmol of 3,4-dihydroxy-3-cyclobutene-1,2-dione was added after the first hour. The reaction was evaporated to dryness in vacuo, then purified by preparative thin layer chromatography on silica gel GF, using 5% methanol in chloroform as a developing solvent. The product was chromatographed a second time using 10% methanol in chloroform as developing solvent. Following extraction of the product from silica gel with chloroform and methanol and evaporation of solvents, 216 mg (68% yield) of pure product was obtained as a blue crystalline solid with a reddish sheen (λ (aq. DMSO):641 nm, ε 221,000).

EXAMPLE 7

Preparation of VI(c) (ii)

1-[4-(diethylamino)-2-hydroxyphenyl]-3-[4-(N-ehtylcarboxymethylamino)-2-hydroxyphenyl]-2,4-dihydroxy-cyclobutenediylium dihydroxide, bis (inner salt) [VI(c) (ii)] was prpared by refluxing with azeotropic water removal equimolar amounts of 3-diethylamino phenol, squaric acid, and N-ethyl-N-3-hydroxyphenyl glycine methyl ester prepared as in Example 6 in 2:1 (v/v) n-butanol: benzene followed by isolation of the monomethylester-dye [VI(c) (i)] by silical gel chromatography. The deep blue methyl ester was hydrolyzed with NaOH to give DECAS [VI(c) (ii)] after acidifaction.

The NHS (N-hydroxysuccinimide) ester of DECAS [VI(c) (iii)] was generated by addition of 1.3 mg of EDAC (1-ethyl-3-(3-dimethylaminopropyl) carbodiimide hydrochloride to a solution of 3.0 mg of DECAS and 0.99 mg of NHS in 120 μl of freshly distilled (CaH2) DMF (dimethylformamide) at 0°. Tlc (silica, 90:10 v/v chloroform: methanol) indicated the presence of the NHS ester of DECAS and disappearance of starting material after 1 hr.

EXAMPLE 8

Preparation of VI(c) (xiii)

To 2.78 mg of acid VI(c) (ii) from Example 7 in 120 μl of dry dimethylformamide was added 1.51 mg of sulfo-NHS (Pierce) followed by 1.27 mg of 1-ethyl-3-(3-dimethylaminopropyl) carbodiimide hydrochloride. The stoppered reaction was stirred by means of a magnetic stir bar. Thin layer chromatography (silica, 90:10 chloroform: methanol vol/vol) showed the gradual disappearance of the blue spot corresponding to VI(c) (ii) and the appearance of a new blue spot ($R_f$=0.2). After 4 hr reaction was judged to be complete. The sulfo-NHS ester VI(c) (iii) was used in solution without further isolation.

EXAMPLE 9

Preparation of XII(c)

5-ethoxy-2-methylbenzthiazole was alkylated in toluene at 65° with ethyl iodide. The resulting salt was condensed with squaric acid at reflux in toluene/butanol with azeotropic removal of H2O to give a blue solution containing XII(c). Purifaction on silica tlc (thinlayer chromatography) eluted with 95:5 $CH_2Cl_2$:$CH_3OH$ gave XII(c) as ablue solid. FLuorescence in 0.01M sodium phosphate, 0.15M NaCl, 0.005M NaN3, 0.01M β-cylclodeextrin, pH7: λ max/ex=651, λ max/em=664 nm.

EXAMPLE 10

Preparation of X 5-methoxy-2,3,3-trimethylindolenine was prepared by condensation of 4-methoxyaniline and 3-hydroxy-3-methyl-2-butanone in 2:1 xylene:butanol at reflux with ZnCl2 catalysis. To 240 mg of 5-methoxy-2,3,3-trimethylindolenine in 10 ml of toluene and 30 ml of n-butanol was added 70 mg of squaric acid. The mixture was refuxed 6 hr with azeotropic removal of H2O. Concentration of the blue solution gave 220 mg of X as green crystals: MS (EI) 456 (M+). Fluoreescence in DMSO containing 0.001M HCl: λ max/em=664.

EXAMPLE 11

Preparation of VI(c) (x)

Condensation of acid VI(c) (ii) from Example 7 (0.27 mmol) and m-aminophenylboronic acid (0.27 mmol) with excess 1-ethyl-3-(3-dimethylaminopropyl)- carbodiimide hydrochloride (≧0.3 mmol) in dry DMF at 5° opver 2 days after silica tlc eluted with 90:10 $CH_2Cl_2$:$CH_3OH$ gave 10 mg of VI(c)(x) having a fluorescence emission maximum of 664 nm when excited >600 nm in DMF.

EXAMPLE 12

Preparation of VI(c)(vi)

To 4.8 mg of amino dye VI(c)(iv) in 2 ml of dry THF in a round-bottomed flask containing a magnetic stir bar was added 1.3 mg of ethyl chlorofumarate (prepared by the method of U. Eisner, G. Elvidge, and A. Linstead, *J. Chem. Soc.*, 1501 (1951)). Then 1.4 μl of triethylamine was added with stirring. Thin layer chromatography (silica, 90:10 toluene:methanol v/v) showed the gradual development of a new blue spot and decrease of starting VI(c)(iv). After overnight stirring, the reaction mixture was purified by preparative thin layer chromatography (tlc) (silica, 90:10 toluene:methanol). The major movign blue band was scraped from the plate and eluted from the silica with methanol. Evaporation of the solvent gave 1 mg of blue residue which was a single spot by thin layer chromatography (as above) and identified as VI(c)(vi) by 300 mHz nmr in CDCl$_3$ with TMS as standard.

EXAMPLE 13

Preparation of VI(c)(iv)

To a solution of 0.27 mmol of VI(c)(iii) in 12 ml of dry dimethylformamide (DMF) at 0° was added dropwise 19.5 mg of ethylenediamine in 1 ml of DMF. A green solution resulted. After 1 hr of stirring at 0° the reaction mixture was stripped of DMF under vacuum. The residue was washed with water and centrifuged. The washing and centrifugation was repeated once. The Rf on silica was 0.23 for VI(c)(iii) and 0.68 for VI(c)(iv) when eluted with 90:10 CH$_2$Cl$_2$:CH$_3$OH (v/v). The crude solid was further purified on preparative tlc eluted with 90:10 CH$_2$Cl$_2$:CH$_3$OH to give 10 mg of VI(c)(iv).

EXAMPLE 14

Preparation of VI(c)(vii)

Acid VI(c)(ii) from Example 7 (219 mg) was dissolved in dry DMF at 0°. N-hydroxy-succinimide (63 mg) was added followed with stirring by 1-ethyl-3-(3-dimethylaminopropyl)carbodiimide hydrochloride (115 mg). After 30 min at 0° followed by 23° for a 4 hr tlc (silica, 90:10 Ch$_2$Cl$_2$:CH$_3$OH) showed a new blue spot, Rf=0.94 and absence of the blue spot for 34, Rf=0.13. To the presumed NHS ester was added a solution of 74 mg of H$_2$NCH$_2$CH$_2$SSCH$_3$ in DMF at 0°. After overnight stirring 0°-5°, tlc (silica, 80:20 ethylacetate:hexane) showed absence of NHS ester. The DMF was removed under vacuum, and the residue was purified by tlc (silica, ethylacetate:hexane 80:20) to give 35 mg of blue solid.

EXAMPLE 15

Preparation of VI(c)(ix)

To a solution of 0.27 mmol of VI(c)(iii) in 12 ml of DMF at 0° was added 31 mg of diethylenetriamine dropwise with stirring. After stirring 1 hr, tlc (silica, 90:10 CH$_2$Cl$_2$:CH$_3$OH) showed absence of VI(c)(iii) (Rf>0.9) and presence of a non-moving blue spot Rf~0. The DMF was then removed under vacuum and the crude blue solid was purified by tlc (silica CH$_3$OH:CH$_2$Cl$_2$ 15:85).

EXAMPLE 16

Fluorescence Data

| Compound | Solvent | $\lambda_{ex}^{max}$ | $\lambda_{em}^{max}$ | φ |
|---|---|---|---|---|
| VI(a)(i) | DMF | 652 | 666 | |
| VI(a)(ii) | toluene | 621 | 632 | |
| VI(a)(v) | methanol | 635 | 652 | 0.79 |

-continued

| Compound | Solvent | $\lambda_{ex}^{max}$ | $\lambda_{em}^{max}$ | φ |
|---|---|---|---|---|
| | PBS | 637 | 658 | 0.26 |
| | PBS/βCD | 653 | 665 | 0. |
| | PBS/SDS | 636 | 658 | 0.23 |
| VI(b)(i) | toluene | 632 | 648 | |
| | methanol | 628 | 648 | |
| | PBS/βCD | 642 | 656 | |
| VI(b)(iv) | methanol | 632 | 651 | |
| | water | 632 | 656 | |
| VI(b)(vi) | methanol | 632 | 651 | |
| | water | 634 | 659 | |
| VI(b)(vii) | methanol | 632 | 652 | |
| | water | 636 | 655 | |
| VI(b)(ix) | methanol | 632 | 652 | |
| | water | 632 | 652 | |
| VI(b)(xiv) | methanol | 631 | 652 | |
| | water | 629 | 650 | |
| | PBS/βCD | 647 | 660 | |
| VII | toluene | 634 | 650 | |
| VI(c)(vii) | toluene | 638 | 653 | |
| | DMF, acid | 648 | 663 | |
| | PBS/βCD | 648 | 662 | |
| | PBS/triton | 648 | 661 | |
| VI(c)(x) | DMF | | 664 | |
| VI(f) | water | 636 | 662 | |
| | methanol/CH$_2$Cl$_2$ | 646 | 664 | |
| | PBS/5% cholate | 648 | 665 | |
| VI(g) | CHCl$_3$ | 640 | 655 | |
| | DMF, acid | 648 | 665 | 0.86 |
| | PBS triton | 647 | 663 | 0.95 |
| | PBS/tween | 643 | 658 | |
| | methanol | | | 0.82 |
| VIII(a) | toluene | 636 | 654 | |
| | CHCl$_3$ | 636 | 654 | |
| VIII(b) | PBS/βCD | 652 | 664 | 1.0 |
| VIII(d) | methanol | 633 | 650 | 0.20 |
| | PBS/βCD | 648 | 660 | 0.25 |
| | PBS | 639 | 659 | 0.02 |
| XIV(a) | toluene | 669 | 679 | |
| | DMF | 674 | 690 | |
| | CHCl$_3$ | 660 | 680 | |
| | PBS/βCD | 676 | 692 | |
| | PBS/γCD | 676 | 692 | |
| XIV(b) | methanol/water | 666 | 672 | |
| IX(a)(i) | methanol | 628 | 639 | 0.11 |
| | DMF | 640 | 656 | |
| | PBS/SDS | 634 | 644 | 0.36* |
| | red cell | 641 | 651 | |
| IX(a)(ii) | methanol | 628 | 639 | 0.10 |
| | PBS/SDS | 633 | 643 | 0.36 |
| IX(a)(vi) | toluene | 641 | 658 | |
| | ethanol | 635 | 645 | |
| | methanol | 629 | 640 | 0.18 |
| | DMF | 640 | 652 | |
| | PBS/SDS | 636 | 645 | 0.48 |
| IX(a)(xiii) | PBS/βCD | 630 | 638 | |
| | PBS/SDS | 634 | 645 | |
| | PBS/CTAB | 639 | 646 | |
| IX(b) | PBS/βCD | 629 | 641 | |
| | PBS/CTAB | 638 | 648 | |
| X | DMSO/acid | 683 | 704 | |
| | PBS/βCD | 650 | 664 | |
| XI | methanol | 650 | 670 | 0.1 |
| XIII | DMSO | 642 | 662 | |
| | PBS/βCD | 647 | 659 | 0.28 |
| | PBS/SDS | 636 | 653 | 0.71 |
| XII(a) | DMF | 674 | 690 | |
| XII(b) | toluene | 682 | 694 | 0.34 |
| XII(c) | PBS/βCD | 651 | 664 | |

"DMF/acid" means DMF acidifed with 5 μl/ml of 1N HCl. "DMSO" means dimethylsulfoxide. "DMSO/acid"" means DMSO acidified with 5 μl/ml of 1N HCl. "PBS" means phosphate buffered saline (10 mM sodium phosphate, 5 mM NaN$_3$, 0.15N NaCl, pH 7. "PBS/βCD" means PBS containing 0.01M β-cyclodextrin. "PBS/SDS" means PBS containing 10 mg/ml of sodium dodecyl sulfate. "PBS/CTAB" means PBS containing 10 mg/ml of cetyl trimethylammonium bromide. "PBS/γCD" means PBS containing 0.01M γ-cyclodextrin. "PBS/Triton" means PBS containing 10 mg/ml of Triton-X-100. "PBS/Tween" means PBS containing 10 mg/ml of Tween-20. "φ" m,eans fluorescence quantum yield. "$\lambda_{ex}^{max}$" means maximum excitation in the fluorescence spectrum. "$\lambda_{em}^{max}$" means wavelength of maximum emission in the fluorescense spectrum. Fluorescense spectra were measured on a Perkin Elmer 650-40 Fluorescence Spectrophotometer.

The invention has been described in detail with particular reference to the above embodiments. It will be understood, however, that variation and modifications can be effected within the spirit and scope of the invention.

What is claimed is:

1. A compound of the formula

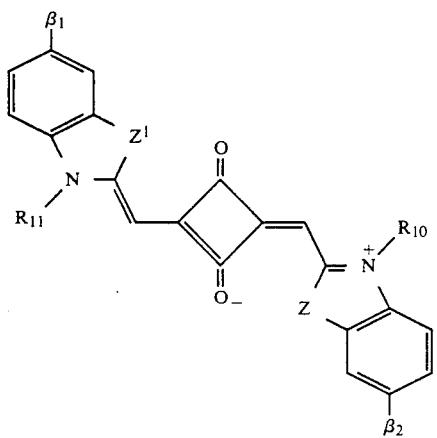

(IV)

wherein:
Z is

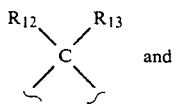

and

Z' is

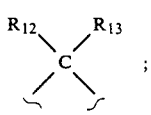

;

$R_{12}$, $R_{13}$, $R_{14}$, and $R_{15}$ are independently hydrogen, lower alkyl (1 to 4 carbon atoms) or $R_{12}$, $R_{13}$ and $R_{14}$, $R_{15}$ are taken together to form

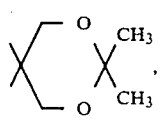

, $R_{10}$ and $R_{11}$ are independently selected from the group consisting of hydrogen, lower alkyl (1 to 4 carbon atoms), alkyl of from 5 to 20 carbon atoms, including cycloalkyl,

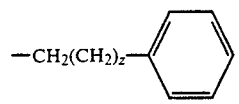

wherein z is 0 to 5,

wherein $R_{21}$ is hydrogen, or lower alkyl (1 to 4 carbon atoms) and v is 0 to 5, and

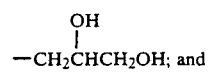

$\beta_1$ and $\beta_2$ are independently hydrogen, halogen selected from the group consisting of chlorine, bromine, and fluorine, or lower alkoxy (1 to 4 carbon atoms), with the proviso that only one of $\beta_1$ or $\beta_2$ is hydrogen or halogen selected from the group consisting of chlorine, bromine, and fluorine when $R_{10}$ and $R_{11}$ are both hydrogen or lower alkyl of 1 to 4 carbon atoms.

2. A compound of the formula

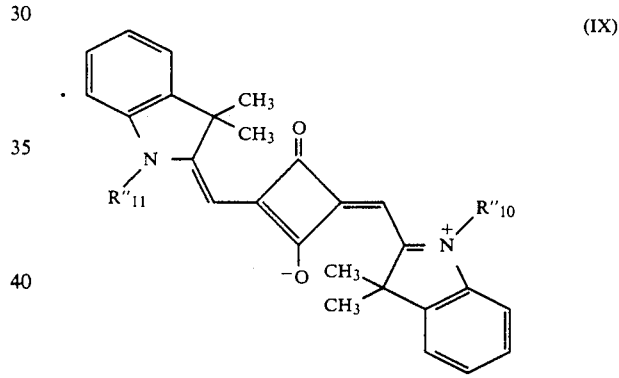

(IX)

wherein:
(a) R"$_{10}$ and R"$_{11}$ are both
(i) —CH$_2$(CH$_2$)$_2$CH$_3$ and one of the phenyl groups has a lower alkoxy substituent,

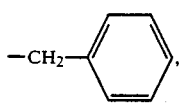

(ii)

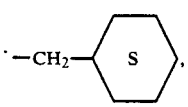

(iii)

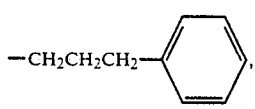

(iv)

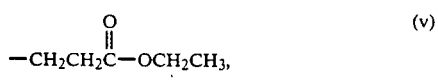

(v)

-continued
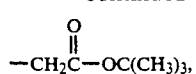 (vi)
 (vii)
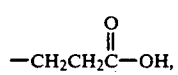 (viii)
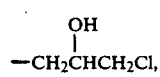 (ix)
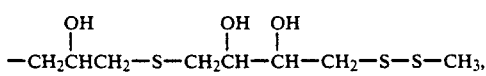 (x)
or
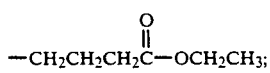 (xi)
or
(b) R"$_{10}$ is
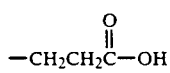
and R"$_{11}$ is
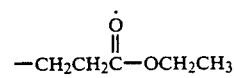
3. A compound of the formula
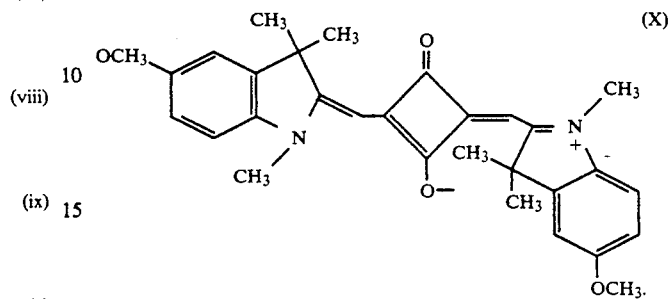 (X)
4. A compound of the formula
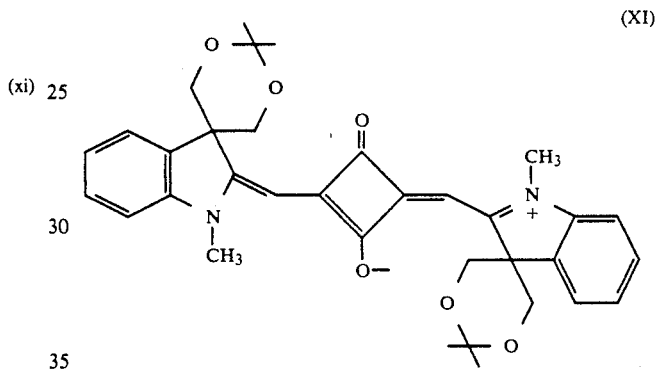 (XI)
* * * * *